(12) United States Patent
Krill et al.

(10) Patent No.: US 6,566,559 B2
(45) Date of Patent: May 20, 2003

(54) PROCESS FOR THE PRODUCTION OF ISOPROPENYL METHYL ETHER

(75) Inventors: Steffen Krill, Hanau (DE); Stephan Kretz, Biebergemünd (DE); Volker Häfner, Langenselbold (DE); Georg Markowz, Karlstein (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 09/871,000

(22) Filed: Jun. 1, 2001

(65) Prior Publication Data

US 2002/0042543 A1 Apr. 11, 2002

(30) Foreign Application Priority Data

Jun. 15, 2000 (DE) .......................... 100 29 599

(51) Int. Cl.$^7$ .............................................. C07C 41/28
(52) U.S. Cl. ................ 568/691; 568/693; 568/667; 568/669; 568/681; 568/682; 568/686
(58) Field of Search ................. 568/667, 669, 568/681, 682, 686, 691, 693

(56) References Cited

U.S. PATENT DOCUMENTS

| | | | |
|---|---|---|---|
| 1,850,836 A | 3/1932 | Guinot | |
| 2,667,517 A | 1/1954 | Longley, Jr. | 260/614 |
| 2,827,495 A | 3/1958 | Bond et al. | 260/616 |
| 2,837,575 A | 6/1958 | Waters et al. | 260/615 |
| 4,469,887 A | 9/1984 | Brockhaus et al. | 562/599 |
| 4,775,447 A | 10/1988 | Hsu et al. | 203/62 |
| 5,013,444 A * | 5/1991 | Mildenberger et al. | 203/43 |
| 5,576,465 A | 11/1996 | Kaufhold | 568/691 |

FOREIGN PATENT DOCUMENTS

| | | | |
|---|---|---|---|
| DE | 26 36 278 A1 | 2/1978 | C07C/43/30 |
| DE | 29 29 827 A1 | 2/1981 | C07C/43/10 |
| DE | 40 39 950 A1 | 6/1992 | C07C/43/15 |
| DE | 195 44 407 | 6/1997 | C07C/41/38 |
| EP | 0 197 283 | 10/1986 | C07C/41/28 |
| EP | 0 415 334 | 3/1991 | C07C/41/38 |
| EP | 0 490 221 A3 | 6/1992 | C07C/41/28 |
| EP | 0 490 221 A2 | 6/1992 | C07C/41/28 |
| EP | 0 703 211 A1 | 3/1996 | C07C/43/16 |

* cited by examiner

*Primary Examiner*—Rosalynd Keys
(74) *Attorney, Agent, or Firm*—Smith, Gambrell & Russell, LLP

(57) ABSTRACT

Process for the production of unsaturated ethers, in particular isopropenyl methyl ether (IPM), by pyrolysis of a ketal-containing or acetal-containing mixture, in particular dimethoxypropane (DMP), in the liquid phase in the presence of an organic carboxylic acid, according to the following reaction scheme:

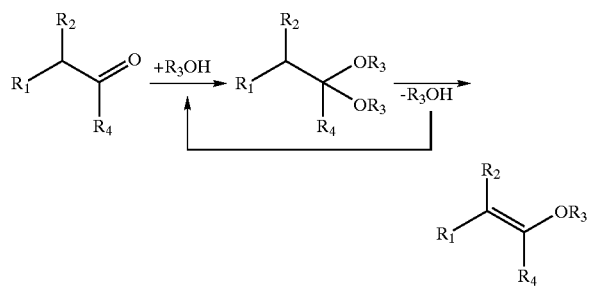

wherein $R_1$=H or alkyl with 1–8 C atoms; $R_2$=H, $CH_3$—, $C_2H_5$—, or Cl—; $R_3$=alkyl with 1–8 C atoms; $R_4$=H, $CH_3$—, $C_2H_5$—, or $C_3H_7$—, and $R_1$ and $R_4$ may be joined to form a 5-, 6-, or 7-membered ring. DMP is produced by the process from acetone and methanol by reaction in an acidic heterogeneous ion exchanger, the product being isolated by extraction with aqueous alkaline solution. In particular the process involves combining the IPM reaction product with the DMP reaction product, which permits the execution of a stable recycling process in which the methanol-containing streams of the IPM and DMP stages can be simultaneously extracted. The product may be isolated by the process by simple distillation of IPM from a mixture containing IPM, DMP and acetone.

11 Claims, 1 Drawing Sheet

PROCESS FOR THE PRODUCTION OF ISOPROPENYL METHYL ETHER

INTRODUCTION AND BACKGROUND

The present invention relates to an improved process for the production of unsaturated ethers, in particular isopropenyl methyl ether, by pyrolysis of a ketal-containing or acetal-containing mixture, in particular dimethoxypropane, in the presence of an organic carboxylic acid.

Various unsaturated ethers are important starting compounds for the production of pharmaceutical products, fragrances and perfumes. Isopropenyl methyl ether (IPM) is such an ether and may be used in particular for synthesizing vitamins, including inter alia the synthesis of vitamin E and vitamin A, and for producing various carotenoids such as astaxanthin and related compounds. IPM may furthermore be used for the synthesis of fragrances and perfumes. In this connection processes are known for the C-3 extension of allyl alcohols or propargyl alcohols, in which at least two equivalents of unsaturated ether are used per mole of substrate. In this reaction, which is also termed the Saucy-Marbet reaction after its discoverers, one equivalent of the ether is used for the C-3 extension of the substrate and one equivalent is used to trap the alcohol produced in situ, with formation of the ketal.

The production of acetals or ketals from the corresponding alcohols and carbonyl compounds, and the production of the unsaturated ethers from the resultant acetals and ketals, is described in the literature. The prior art is discussed here separately for ketalization and ketal pyrolysis for the production of the unsaturated ethers. It is generally known that dimethoxypropane (DMP) can be prepared from acetone and methanol by reaction in the presence of an acid catalyst.

Lorette et al., J. Org. Chem., 1959, p. 1731, describes the dependence of the educt stoichiometries and the temperatures on the kinetics of this reaction, in particular the fact that the equilibrium of this reaction is displaced predominantly towards the educts and accordingly it is not possible under moderate conditions to achieve a complete educt conversion. It is found that in order to achieve good educt conversions, low temperatures, i.e. down to −30° C., have to be established, with an acetone/methanol ratio of 1:2 to 1:4. The ketalization of Lorette et al. is performed in the presence of acidic ion exchangers, the reaction being carried out as a fixed bed catalysis reaction. The working up of the product solution that is produced, the water content of which is between 3 and 4 wt. %, is complicated due to the formation of azeotropes between DMP and methanol on the one hand and acetone and methanol on the other hand, and the yields of isolated DMP are correspondingly low due to the losses.

U.S. Pat. No. 2,827,495 of Bond et al. is concerned with the working up of the aqueous, methanolic product mixture by extraction with aqueous alkali, in particular sodium hydroxide in a concentration between 13 and 16 wt. %. By this process, which is carried out industrially as a countercurrent extraction process, a methanol-free, almost pure DMP (97%) can be obtained as organic product of the extraction in an outstanding extraction yield (>99%, see Example IV of the cited patent). Nevertheless, the DMP extracted in this way still contains about 1.5 wt. % of water, which in molar terms corresponds to a ratio of 8:92. This mixture cannot however be used to produce IPM in large yields since the water that is present reacts quantitatively with DMP during the pyrolysis, in the presence of an acid catalyst, to form acetone and methanol. The further product purification and the use of the resultant DMP for the production of IPM is not described.

In U.S. Pat. No. 1,850,836 of Guinot et al. two basic possibilities for the production and isolation of acetals are already described, namely the reaction of an aldehyde with an alcohol in the presence of a catalytic amount of a mineral acid, in particular gaseous HCl. After the reaction equilibrium has been established the reaction mixture is neutralized with an amount of base at least equivalent to the acid (in order to suppress the reverse reaction during the working up) and is then worked up by adding an aliphatic auxiliary solvent that is water-insoluble and forms a minimum temperature azeotrope with the alcohol that is used. In this way the nonpolar acetal can be freed by means of the non-water-soluble aliphatic solvent from water and largely from the alcohol, and the alcohol can then be extracted as an azeotrope with the aliphatic compound. It is obvious that considerable amounts of aliphatic compounds are required for the complete removal of the alcohol, following which an aqueous extraction is necessary to separate the methanol from the aliphatic solvent. Overall the process is complicated and is not particularly suitable for industrial application.

In U.S. Pat. No. 2,837,575 of Waters et al. a ketalization with gaseous HCl is described. In order to increase the acetone conversion, up to 8 wt. % of HCl is used, which then has to be neutralized with sodium hydroxide, and a not inconsiderable amount of salt is formed. The subsequent working up is performed by two complicated extractions with sodium hydroxide of different concentrations followed by an additional extraction with a readily volatile aliphatic hydrocarbon. It is clear from the large number of necessary separation operations that the process is not suitable for an economic industrial application.

After the implementation of the ketalization per se had been technically solved by the publication by Lorette et al., J. Org. Chem., 1959, p. 1731, using a stable, acidic ion exchanger, the subsequent relevant patent publications were accordingly only concerned with the recovery of the complex product mixture, which due to the presence of water tends to undergo a reverse reaction and thus complicates the recovery still further.

According to the process described in DE-OS 26 36 278, Zinke-Allmang et al., BASF, the reaction of alcohol and carbonyl compound is carried out in the presence of gaseous HCl and at least equivalent amounts of calcium sulfate as water-binding agent. The same authors concede however in a later publication, DE 29 29 827, Zinke-Allmang, BASF, that this does not represent an optimal solution to the problem, since considerable amounts of the water-binding agent are used and have to be recovered. DE-OS 29 29 827 describes the reaction in an excess of acetone with an acetone/methanol ratio of 3.6 to 4.4, and recovery in a distillation column with 40–60 trays. The azeotrope of acetone and methanol is recycled at the head of the column and a mixture of DMP and water is extracted in a side stream, following which DMP can be obtained after phase separation. In this procedure however an only approximately 4 wt. % DMP mixture with a water content of ca. 0.5 wt. % is produced due to the establishment of the equilibrium. It is clear that almost 95 wt. % of the unreacted product solution has to be distilled off in order to isolate the product, which makes the process extremely energy-intensive, and the spatial requirements of the necessary distillation column can be extremely large, having regard to the recycling required for a clean separation.

U.S. Pat. No. 4,775,447 describes a process for the production of DMP, in which an acidic heterogeneous ion exchanger is likewise used as catalyst and the ratio of acetone to methanol is adjusted to between 1:1 and 1:3. The recovery according to this procedure is however extremely complicated and involves a first distillative removal of an acetone-rich azeotrope of acetone and methanol. A corresponding amount of acetone must be added to the remaining mixture of methanol and DMP so that, in a second distillation, an azeotrope of acetone and methanol of the composition (ca. 86 vol. % acetone and 14 vol. % methanol) is removed. The patent does not discuss the acetone-methanol separation. Also, the separation from the DMP of the water formed in the reaction is not described.

The distillative separation as well as the complex azeotropes in the water-DMP-acetone-methanol system are described in Brunner and Scholz, Chem. Ing.-Tech. 52 (1980), No. 2, pp. 164–166, as well as in Beregovikh et al., Khim. Farm. Zhl. 17 (1983), pp. 454–459.

Brunner and Scholz question the earlier results of Lorette et al. concerning the existence of a ternary azeotrope of acetone, methanol and DMP. Brunner and Scholz come to the conclusion that an acetone-rich azeotrope (composition as described above) of acetone and methanol having a boiling point of 55.4° C., as well as a further azeotrope of methanol and DMP having a boiling point of 61.0° C. and a composition of 72.5 mole % of methanol and 27.5 mole % of DMP exist.

The production of unsaturated ethers from the corresponding acetals or ketals is also described in the literature. U.S. Pat. No. 2,667,517 describes the pyrolysis in the presence of an acid catalyst from the group comprising sulfonic acids, in a hydrocarbon or a chlorinated hydrocarbon as solvent and/or diluent. Problems arise however in this procedure due to the high boiling point compounds that are formed in the reaction, which contaminate the catalyst solution and necessitate a high discharge rate. EP-A 0 197 283 describes the use of a mineral oil that is combusted after use, which however involves a not inconsiderable specific consumption of the catalyst.

It is also possible to operate in the absence of a solvent if, as proposed in DE-A 40 39 950, the pyrolysis is conducted at elevated temperatures up to 200° C. in the presence of a catalyst system comprising an acid on the one hand and an amine on the other hand. The process is not generally applicable and has the disadvantage that here too the catalyst phase is contaminated by the non-selective reaction and thermal lability of the substances that are employed, which again necessitate a discharge.

EP-A 0 703 211 suggests a solution to these problems. By using high boiling point branched organic acids, the reaction can be carried out at temperatures between 100° C. and 250° C., whereby only a few high boiling point byproducts accumulate in the catalyst solution due to the highly selective nature of the reaction, which have only a slight influence on the catalytic activity of the system.

Sterically demanding substituted neoacids with 9 or more hydrocarbon atoms are used as preferred acids. The working up of the complex product mixtures of IPM, methanol, DMP and acetone is not discussed. It is also not clear what effect the water entrained with the DMP that is fed in has on the catalytic activity.

A common feature of all these processes is that the isolation of the product mixture is greatly complicated on account of the azeotrope with methanol that is formed during the distillation, and in addition there is also a back-reaction of DMP with water unless appropriate measures are adopted (distillation under basic conditions, column provided with Ca(OH)$_2$), which however also represents a considerable expense. In the processes listed in the prior art a high product purity is always particularly sought after in the isolation of the ketal, since on account of the water that is fed in together with DMP into the pyrolysis (IPM) stage there is a back-reaction of the ketal to the corresponding alcohol and the carbonyl compound.

In particular, none of the proposed processes considers how to connect the DMP and IPM stages in a practicable manner. This is particularly important against the background that byproducts of the DMP stage have a significant influence on the service life of the catalyst used in the IPM stage. In particular, no process has hitherto been described that envisages connecting the two process stages by simplifying the complex working up caused by the azeotropes.

Since up to now no process is known that describes the production of unsaturated ethers and their precursors, the corresponding ketals and acetals, with recycling of all unreacted substances, the object of this invention was accordingly to provide a process for the production of unsaturated ethers in which the high level of byproducts in the ketal pyrolysis can be tolerated.

A further object of this invention was to provide a process that also tolerates byproducts as well as the pyrolysing ketal in the thermolysis stage.

A particular object of this invention is a process that can operate in the DMP extraction without the addition of a foreign substance, for example an aliphatic hydrocarbon that forms a minimum temperature azeotrope with methanol, and that moreover permits a simple isolation of the unsaturated ether from the methanol-containing and optionally acetone-containing product solution of the pyrolysis.

A further object of this invention was to produce the corresponding ketal(DMP) in high selectivity and yield starting from acetone and methanol and to pyrolyse in a connected process step DMP as well as acetone to the desired product IPM, wherein the separation of water, which greatly interferes in the DMP pyrolysis, should not take place by adding an extraneous additional auxiliary substance.

SUMMARY OF THE INVENTION

The invention provides an improved process for the production of unsaturated ethers from the corresponding ketal precursors, the production of these ketal precursors by ketalization of the corresponding carbonyl compound and an aliphatic alcohol, and the advantageous recovery of the product stream of this ketalization by combining it with the product stream of the ketal pyrolysis, followed by extraction of the combined organic product streams with an aqueous sodium hydroxide solution in order to recover unreacted carbonyl compound and/or alcohol.

In particular, this invention is a process for the production of unsaturated ethers of the formula (1)

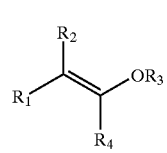

(1)

by pyrolysis of acetals or ketals of the general formula (2)

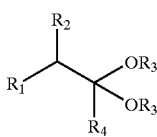
(2)

wherein $R_1$=H or alkyl with 1–8 C atoms; $R_2$=H, $CH_3$—, $C_2H_5$—, or Cl—; $R_3$=alkyl with 1–8 C atoms; $R_4$=H, $CH_3$—, $C_2H_5$—, $C_3H_7$—, and R, and $R_4$ may be joined to form a 5-, 6-, or 7-membered ring, characterized in that a.) the corresponding acetal or ketal of the formula (2) formed from the corresponding alcohol of the general formula (3)

wherein $R_3$ denotes space-holders for the substituents $R_3$ specified above, and from an aldehyde or ketal of the general formula (4)

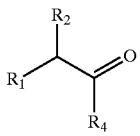
(4)

wherein $R_1$, $R_2$ and $R_3$ denote space-holders for the substituents $R_1$, $R_2$ and $R_3$ mentioned above, is ketalized in the presence of an acid catalyst and b.) the product stream resulting from the ketalization, which consists of a mixture of the components of the formulae (2), (3), (4) and water, is combined with the product stream of the ketal (or acetal) pyrolysis, which consists of ketal (or acetal), the desired unsaturated ether of the formula (1) as product, and the alcohol of the formula (3), and c.) the combined organic product streams are extracted with an aqueous alkaline solution and the organic product stream of this extraction, which consists of a mixture of the corresponding ketal or acetal, the desired unsaturated ether as product, and residual amounts of the aldehyde or ketone of the formula (4) and water, and d.) the desired end product is isolated from this largely alcohol-free organic heteroazeotrope product stream by means of distillation, and e.) the distillation residue, which contains the acetal of the formula (2) and the corresponding carbonyl compound of the formula (4), is pyrolyzed in a high boiling point organic carboxylic acid at 80° C.-300° C. and the product stream formed thereby, which in addition to the desired ether also contains unreacted ketal and/or acetal and the corresponding alcohol, is fed to the extraction described under b.) and combined with the organic product stream from the ketalization.

Examples of unsaturated ethers of the formula (1) are isopropenyl methyl ether, isopropenyl ethyl ether, isopropenyl propyl ether, isopropenyl isopropyl ether, isopropenyl propyl ether, isopropenyl butyl ether, ethenyl methyl ether, ethenyl ethyl ether, ethenyl propyl ether, ethenyl isopropyl ether, propenyl methyl ether, propenyl ethyl ether, propenyl propyl ether, propenyl isopropyl ether, propenyl butyl ether, wherein isopropenyl methyl ether is particularly preferred.

Examples of acetals or ketals of the formula (2) are dimethoxypropane, acetaldehyde-dimethylacetal, acetaldehyde-diethylacetal, acetaldehyde-diisopropylacetal, acetaldehyde-dipropylacetal, propionaldehydedimethylacetal, propionaldehyde-dipropylacetal, propionaldehyde-diisopropylacetal, butyraldehyde-dimethylacetal, butyraldehyde-diethylacetal, butyraldehyde-dipropylacetal, butyraldehyde-dibutylacetal, and corresponding acetals and ketals of aldehydes and ketones mentioned hereinafter of the general formula (4), dimethoxypropane being preferred.

Examples of aliphatic alcohols of the formula (3) are methanol, ethanol, propanol, isopropanol, butanol, pentanol, isopentanol, hexanol, heptanol and octanol, methanol and ethanol being particularly preferred.

Examples of aldehydes and ketals of the formula (4) are acetone, acetaldehyde, propionaldehyde, butyraldehyde, isobutyraldehyde, valeraldehyde, isovaleraldehyde, hexanal, ethylhexanal, methyl isopropyl ketone, methyl ethyl ketone, diethyl ketone, ethyl isopropyl ketone, methyl isobutyl ketone, acetone being preferred.

BRIEF DESCRIPTION OF THE DRAWING

The present invention will be further understood with reference to FIG. 1 which is a flow diagram of the process of the invention.

DETAILED DESCRIPTION OF INVENTION

Figure 1:
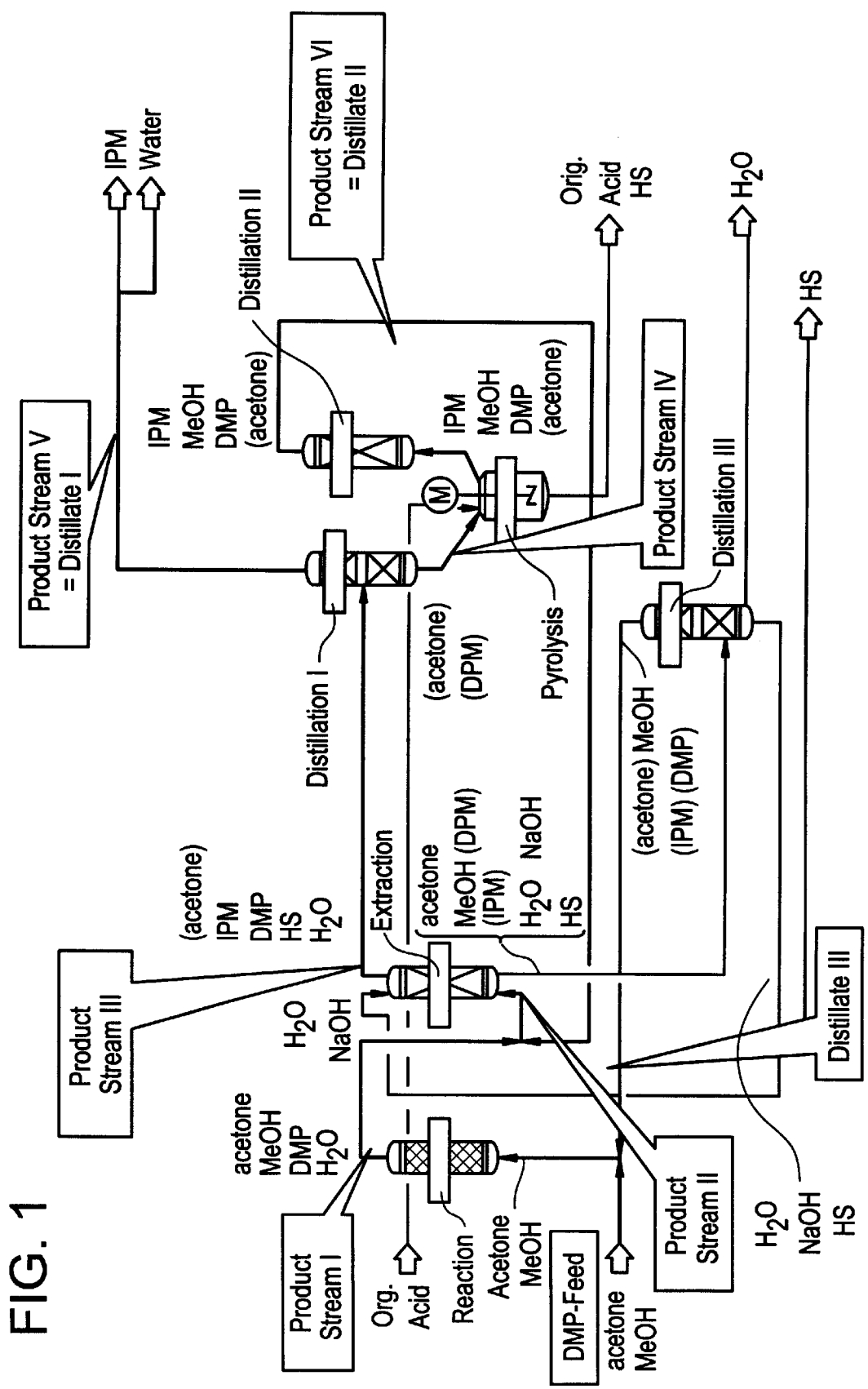

A preferred embodiment of the process according to the invention is outlined in FIG. 1, the connection of the individual process operations being given purely by way of example without any claims to completeness regarding the illustration of the possible combinations. The product streams I–VI in FIG. 1 refer to the following process stages:

DMP Feed=feed stream of the DMP reaction
product stream I=ketalisation
product stream II=combined organic phases
product stream III=extraction stream
product stream IV=DMP pyrolysis feed stream
product stream V=IPM pure distillation (distillate I)
product stream VI=pyrolysis stream (distillate II), and
HS=high boiling point compounds.

The process of this invention solves in a simple manner the long-standing problem in the prior art concerning the production of DMP from acetone and methanol and the production of IPM from DMP, namely the problem of isolating DMP, in particular the separation of water and methanol, and the isolation of IPM, in particular the separation of methanol from the pyrolysis solution (product stream VI).

By extracting the combined product streams I and VI of the reaction solutions, an organic product stream III can be produced with a high degree of efficiency that is almost methanol-free and that contains the two desired products, namely DMP and IPM, as well as acetone and traces of water. By simple distillation (distillation I) the water-IPM and methanol-IPM azeotropes and the total amount of IPM can now be obtained as distillate I, the heteroazeotropes being separated at the head of the distillation column. In this way it may be ensured that an anhydrous mixture of DMP and acetone is reacted with a high degree of selectivity in the pyrolysis reaction without a back-reaction of DMP to methanol and acetone occurring.

This process accordingly provides a technical solution for the continuous production of IPM and DMP, in which unreacted starting substances can be fully recycled and in this sense do not constitute specific consumptions. The recovery takes place without the need to add an auxiliary solvent for the separation of the methanol-containing azeotropes. The technical process will be described in detail hereinafter.

The first feature of the invention relates to a process for the production of ketals, in particular DMP, by preparation from the corresponding carbonyl compound and the corresponding alcohol with condensation of water of reaction in the presence of an acidic ion exchanger, the removal of the alcohol, and the isolation of the DMP from the DMP-containing product stream I by combining the DMP product stream I with the product stream VI from the pyrolysis stage, and the extraction of the combined organic streams with aqueous alkaline solution.

In the simplest case of the process according to the invention an aqueous alkaline solution is used for the extraction that frees the combined organic product streams I and VI from the DMP and IPM production more or less completely from methanol, acetone and water of reaction. An organic product stream III that comprises DMP and IPM and contains only minor concentrations of water and methanol is formed as a result of this central extraction step.

The second feature of the process according to the invention relates to the isolation of IPM by the distillation I of the organic product stream III occurring after the alkaline solution extraction, which product stream substantially consists of DMP and IPM and may contain acetone as principal subsidiary component (depending on the degree of extraction the acetone content may however be drastically reduced) and contains in relatively small concentrations water (<2%) and methanol (<5%), wherein a.) an azeotrope of IPM and methanol and a further azeotrope of IPM and water and pure IPM are formed as distillate I, and b.) this distillate I (product stream V) after condensation is separated into two phases, the upper phase of which contains more or less pure IPM in a concentration of between 90 and 100% and the lower phase consists of water and methanol, and c.) an organic product stream IV is obtained as distillation residue, which is more or less free of water and methanol and consists of DMP in addition to acetone.

The third feature of the process according to the invention relates to the pyrolysis of DMP-acetone mixtures by reacting the DMP solution occurring after the IPM distillation I (product stream IV) with an organic carboxylic acid at elevated temperatures, characterized in that a.) a solution is formed as distillate II that consists of unreacted DMP, acetone and the reaction products isopropenyl methyl ether and methanol, and b.) the acetone fed to the pyrolysis stage behaves inertly compared to processes with sulfonic acids and does not react, or contributes to the formation of byproducts, in particular high boiling point products, and c.) an organic carboxylic acid with a boiling point >80° C., in particular with a substituent in the alpha-position to the carboxylate group, which ensures sufficient stability under the reaction conditions, is used as catalyst acid, and d.) the product stream VI of the pyrolysis, consisting of IPM-acetone-methanol and unreacted DMP, is combined with the organic product stream I from the DMP production and is then worked up in the alkaline solution extraction.

The reaction is carried out at different temperature levels in the various stages in order to achieve a high selectivity and high conversion rates.

The first process step relates to the production of DMP from acetone and methanol by ketalization (product stream I) and discharge of water. The formation of DMP from methanol and acetone takes place at temperatures from −40° C. to 40° C., a preferred embodiment being carried out between 0° C. and −30° C. Although higher temperatures (1° C.-40° C.) are also suitable for carrying out the reaction, on raising the temperature of the reaction or when using a large excess of acetone, only a low concentration of DMP is obtained in the product solution and the recovery is accordingly more complicated and costly. High product selectivities can be achieved at lower temperatures, and no formation of byproducts, in particular aldolization of acetone to mesityl oxide and the corresponding β-hydroxyketone is observed in the reaction.

The reaction times in this temperature range are sufficiently fast for the process to be carried out on an industrial scale to produce a DMP solution (product stream I) containing up to 25 wt. % of DMP. In addition to the temperature, the stoichiometry of the educts acetone in relation to methanol also has a decisive effect on the acetone conversion and thus on the DMP concentration in the product stream I. In general an educt ratio of acetone to methanol of between 5:1 and 1:5 is established, in which connection it is evident from the Law of Mass Action that a methanol-rich procedure is preferred. Normally an educt ratio of between 1:1 and 1:4 is preferred.

Acidic ion exchanger resins are usually used as catalyst for the conversion, in which the acidity is generated by —$SO_3H$ groups covalently bound to a carrier resin. A good catalytic activity combined with good catalyst service lives are achieved with Amberlyst ion exchangers (Rohm & Haas) and Dowex catalysts (The Dow Chemical Co.). After appropriate activation the catalysts are preferably packed into suitable columns, the process being carried out in a continuous manner. The catalysts are regenerated in a simple manner by reactivation with mineral acids after loss of catalytic activity.

The next process step involves the combination of the product streams I and VI with the organic product stream II, i.e. the organic product stream I of the production of DMP from acetone and methanol and the reaction product of the product stream VI of the DMP pyrolysis. After combining these organic product streams a solution is formed (product stream II) that contains the main components methanol, acetone, DMP, IPM and water. The resulting product stream II, which passes to the extraction, is characterized by the fact that methanol, acetone, DMP and IPM are present in concentrations of in each case >5 wt. % and the water content of the phase is <5 wt. %. It is obvious that the methanol and acetone contents are determined primarily by the composition of the DMP feed of the DMP reaction. In a preferred procedure with an acetone:methanol ratio of 1:2 to 1:4 and a reaction temperature <0 C. (product stream I then contains >10 wt. % DMP) and a DMP conversion rate of >75% in the DMP pyrolysis, a product stream II that has a (methanol+acetone) content of 50 wt. % or more is passed to the extraction.

The combination of the product streams I and VI is followed by the extraction with aqueous alkaline solution, in which the organic product stream II is brought into contact with an aqueous alkaline solution in a concentration of 1–30 wt. % of the corresponding hydroxide compound.

The volume ratio of the organic phase to the aqueous phase is between 1/20 to 2. The extraction may in the simplest case take place by stirring the organic phase once or several times with the aqueous phase. After phase separation the ketal-containing IPM phase can be contacted again with alkaline solution depending on the desired degree of extraction. For an industrial-scale reaction the extraction is preferably carried out as a continuous countercurrent extraction, wherein the organic phase at the bottom of the column is added to a suitably dimensioned extraction column and comes into contact in countercurrent with an aqueous alkaline solution added to the head of the column.

The countercurrent extraction with alkaline solution has the following objectives, which can be achieved by optimal adjustment of the extraction parameters:

a.) separation of methanol from the product streams I and VI from the DMP production and IPM production;

b.) separation of water and methanol from the product streams I and VI from the DMP production and IPM production in order to prevent back reaction of DMP or IPM to acetone and methanol;

c.) separation of unreacted acetone for recycling to the DMP reactor.

The extraction may however also be carried out with flow-through mixer-settler units connected in series, the organic phase and aqueous phase likewise being contacted in countercurrent. In the simplest case the extraction is carried out at moderate temperatures, in particular at room temperature.

Aqueous solutions of KOH and NaOH may be used as alkaline solutions, a concentration of between 1 and 30 wt. % of the corresponding alkali metal hydroxide being adjusted. Normally the concentration of the alkaline solution is adjusted to be between 10 and 20 wt. %, the extraction taking place in a significantly simpler manner in the presence of IPM in order to obtain the ketal, in contrast to U.S. Pat. No. 2,827,495, since IPM is used as a non-polar extraction agent and increases the efficiency of the extraction. The process enables both IPM and DMP to be recovered at a recovery rate of >95% in the organic extraction phase (product stream III), no noticeable back-cleavage of the components being observed.

Normally after the extraction an organic product stream III is obtained that is more or less free of methanol and simply has a methanol content of <1 wt. %. Also, the water content in the product stream III can be reduced to significantly below 1 wt. % by appropriate extraction. The water content of the product stream III is however less critical, since due to the presence of IPM in the subsequent distillation it is possible to remove water efficiently as an azeotrope with IPM and thus to suppress efficiently the back reaction in the DMP pyrolysis (IPM production).

The working up of the organic substrates, in particular acetone and methanol, that are contained in the aqueous phase after the extraction with alkaline solution is carried out by simple distillation III of the components, in which methanol and acetone may be added again to adjust the desired stoichiometry of the DMP reaction.

The distillation I of the product stream III, the composition of which has already been described, is carried out on the one hand in order to isolate pure IPM, such as can be used for most applications as a substrate in organic reactions, and on the other hand to produce a DMP of suitable product quality that is required in order to carry out the pyrolysis for the production of IPM. A suitable DMP quality in this connection substantially means the absence of water in the product stream IV used as feed for the pyrolysis stage.

The distillation I of the product stream III with the production of the distillate I (product stream V) is substantially determined by the azeotropes with IPM formed as distillate I. On the one hand a heteroazeotrope of IPM and water is obtained with a molar composition $IPM:H_2O=91:9$ (i.e. 2.4 wt. % of water in IPM) having a boiling point of 34.1° C. (1.013 bar), and on the other hand an azeotrope of IPM with methanol is obtained having a composition of ca. 6 wt. % of methanol and a boiling point of 33.9° C. Both the azeotropes and pure IPM are condensed as distillate I (product stream V) from the pure IPM column, two phases being formed. The upper organic phase contains IPM in a purity of >95%, normally >97%, though depending on the number of stages of the distillation I and acetone content in the product stream III a specific acetone concentration can also be adjusted.

By removing water and methanol as IPM azeotropes, an organic product stream is produced at the bottom of the distillation column (product stream IV) that consists substantially of a mixture of DMP and acetone and thus for all practical purposes no longer contains water or methanol. This organic product stream IV constitutes the feed of the pyrolysis stage and is converted by contact with the organic catalyst acid into IPM and methanol. The product stream IV is characterized substantially by an acetone content of <50%, a (water+methanol) content of less than 2%, and consists mainly of DMP (content: >50%). Higher acetone contents are also tolerated in the pyrolysis stage, but are actually not desirable in order to achieve good space-time yields.

The pyrolysis of the organic product stream IV is carried out according to the invention by reacting in the liquid phase an acetone-containing DMP solution (product stream IV) in an organic carboxylic acid. The advantages of using organic carboxylic acids compared to the use of mineral acids as catalysts are substantial, since the last-mentioned catalysts can only be used in a suitable inert solvent. The carboxylic acids according to the invention one the other hand may permit, by optimal adjustment of the parameters of reaction temperature and residence time (which may be adjusted by the metering of the DMP feed), a highly selective reaction of DMP to IPM, may enable a high degree of conversion to DMP to be established, and finally the organic carboxylic acid only has a slight tendency to form high boiling point compounds and can be used in bulk.

The type of carboxylic acid can be varied within wide ranges, and monocarboxylic, dicarboxylic or oligocarboxylic acids may be used as long as it is ensured that the reaction can be carried out in liquid homogeneous phase. Either the organic carboxylic acid is dissolved in an inert solvent, or it has a melting point that is below the reaction temperature. Preferably carboxylic acids are used that have a boiling point between 80° C. and 350° C.

The organic carboxylic acids used in the present process are preferably aliphatic, alicyclic, aromatic carboxylic acids with 5 to 20 hydrocarbon atoms, in which the hydrocarbon radical may carry one or more functional groups. Valeric acid and higher homologues are particularly preferred as carboxylic acid. Examples of branched derivatives that may be used are isobutyric acid, pivalic acid and neopentylcarboxylic acid.

Examples of aromatic, substituted and unsubstituted carboxylic acids are benzoic acid, m-chlorobenzoic acid and p-nitrobenzoic acid, or also monoterephthalic acid. Halogenated derivatives such as for example trihalogenated acetic acid (trichloroacetic acid, trifluoroacetic acid) may also be used.

It is particularly preferred to use acids that have a sufficiently high boiling point so that, depending on the reaction temperature that is adjusted, they do not distil over with the IPM-containing product (product stream VI). The acids may however optionally boil under reflux.

A further feature of the process according to the invention is that the carboxylic acids used as catalyst in the pyrolysis form, under prolonged reaction times, esters with the alcohol that is released, with the result that without discharge there is a noticeable increase in the corresponding ester in addition to the carboxylic acid, without however any pronounced influence on the yield and conversion rate of the reaction being observed. By way of example there may be mentioned the catalyst esterification with the formation of methyl 2-ethylhexanoate when using 2-ethylhexanoic acid in the pyrolysis of DMP.

The weight ratio of ester to acid may be varied within wide limits up to 95:5, the pure acid without any ester naturally being present at the start of the reaction.

The ratio can be kept at a constant level by discharging the ester that is formed and replenishing the carboxylic acid. The mixture of ester and acid may however also be removed by batchwise discharge, with a noticeable drop in the conversion, if the aforedescribed ratio is exceeded. It is possible to recover the acid from the corresponding ester by simple saponification and to recycle it to the reaction.

Depending on the execution of the reaction, the distillate II and the product stream VI can be withdrawn at the head of a single-stage or multistage distillation column. Particularly preferred are carboxylic acids that are branched in the alpha-position to the carboxylate group, such as for example 2-ethylhexanoic acid. As representatives of the so-called neoacids, such as are also obtained in the Koch synthesis, there may be mentioned at this point pivalic acid, neooctanoic acid, neodecanoic acid and 2,2,5-trimethyldecanoic acid. A criterion for the choice of a suitable acid is, inter alia, as large a temperature range as possible in which the catalyst exists in liquid form. Unbranched carboxylic acids that are not mentioned in EP 0 703 211 may also be used in the process according to the invention.

A particular advantage of using organic carboxylic acids compared to the mineral acids described in the literature is the fact that a substantial acetone concentration in the product stream IV is tolerated without there being any formation of high boiling point byproducts that would necessitate a high discharge rate. As mentioned above, it is preferred to operate the process in the absence of a further solvent, even though this embodiment may be expedient with certain substrates. The temperature of the pyrolysis may be varied within wide limits and is normally adjusted between 80° C. to 300° C.

The process according to the invention has an IPM selectivity of at least 90%, preferably at least 95% and particularly preferably an IPM selectivity of more than 95%.

After eliminating methanol from DMP a product stream VI is obtained at the head of the distillation column II that is directly connected to the pyrolysis unit, which principally consists of IPM and methanol and unreacted DMP. Depending on the product stream IV the product stream VI also contains acetone, which behaves inertly during the reaction. Normally a pyrolysate is obtained that is characterised by the following composition:

| IPM: | <60 wt. % |
| DMP: | <50 wt. % |
| methanol: | >10 wt. % |
| acetone: | <50 wt. % |

Product stream VI is combined with the DMP solution (product stream I) after the ketalization and is worked up further as described above.

The purity of the IPM isolated by the process according to the invention corresponds to a product quality that is necessary for use as an educt for synthesising intermediates for the synthesis of vitamin E, vitamin A and various carotenoids.

Experimental Part

EXAMPLE 1

Pyrolysis of the DMP-acetone solution (product stream IV) with 2-ethylhexanoic acid as catalyst:

The liquid catalyst acid 2-ethylhexanoic acid (2-EHS, 314.1 ml; 283.6 g) is placed in a double-walled glass vessel equipped with a mechanical stirrer and externally heated via a thermostatically controlled heater. The glass reactor is connected to a 5-tray bubble cap column (internal diameter: 50 mm), via which the vapour-phase reaction products are rectified. DMP-containing product stream IV consisting of the following components is metered in through a capillary:

| IPM: | / wt. % |
| DMP: | 94.0 wt. % (= 41.64 mole) |
| Acetone: | 5.0 wt. % (= 3.97 mole) |
| Water: | 1.0 wt. % (= 2.56 mole) |

The catalyst acid is heated to a reaction temperature of 130° C., and an LHSV (Liquid Hourly Space Velocity) of 0.59 l feed/h/$1_{2-EHS}$ is adjusted at a constant reflux ratio of 1:1. A mixture of unreacted DMP, IPM, methanol and acetone is condensed at the head of the column and the quantitative composition is determined by gas chromatography. A total of 5440 ml of the product stream IV are metered in over a period of 29.2 hours. After condensing the vapours, 4591 g of distillate II are obtained having the following composition:

| IPM: | 41.7 wt. % (= 26.55 mole) |
| DMP: | 26.2 wt. % (= 11.54 mole) |
| Acetone: | 8.2 wt. % (= 6.5 mole) |
| Methanol: | 23.2 wt. % (= 33.22 mole) |
| Water: | / wt. % |

The conversion of DMP is 72.3%, the conversion referring to two reactions, namely a.) the back-cleavage of DMP with water to form acetone+methanol, and b.) the desired reaction to form IPM. The IPM selectivity is 96.4% and refers only to DMP that has not been back-cleaved with water. No byproducts are detected. The condensate from the pyrolysis (product stream VI) can be combined directly with the DMP reaction solution (product stream I) and worked up in the extraction.

The example shows that with incomplete separation of water, under pyrolysis conditions the quantitative back-reaction of DMP and IPM with water leads to acetone and methanol with a virtually selective conversion of DMP to IPM.

EXAMPLE 2

Reaction of methanol with acetone at low temperatures in the presence of an acidic ion exchanger (generation of product stream I), combination with product stream VI (pyrolysis stream from the DMP pyrolysis), extraction of the product stream II with aqueous sodium hydroxide solution and distillation I of the resulting IPM-DMP-acetone-containing product stream III.

A glass column (internal diameter: 27 mm, length: 100 cm) that can be cooled with a double-walled jacket is packed with an acidic and a basic ion exchanger that have previously been activated and purified according to described methods. 250 g of DOWEX 50 (acidic; density 0.73 g/ml;= 280.4 ml) are used as acidic ion exchanger and 59.5 g of DOWEX 1 (density: 0,58 g/ml=103 ml) are used as basic ion exchanger. The ion exchanger zone is cooled to −20° C. with a cryostat and a solution of acetone and methanol in a molar ratio of 1:4 is cooled to room temperature and then pumped into the reactor. 0.44 kg of the educt solution is pumped into the reactor for 5 hours, corresponding to a WHSV (Weight Hourly Space Velocity) of 1.57 kg feed/h/l (referred to the active acidic ion exchanger). The resulting product stream I contains in addition to unreacted educts the reaction products water and DMP. An IPM-containing organic stream (product stream VI) formed in the DMP pyrolysis in order to produce IPM, is metered to this product stream I. The metering rate of product stream VI is 0.176 g/h.

A product stream II is formed that is extracted in countercurrent with aqueous sodium hydroxide (17.3 wt. % NaOH) in a mechanically stirred column (manufacturer: Kühni). The extraction is carried out so that the aqueous sodium hydroxide solution forms the continuous phase and the organic product stream II forms the dispersed phase. An organic product stream III is obtained at the head of the extraction column, which is almost free of methanol and water and contains only a very small amount of acetone.

The feed rate of the organic product stream II, which is added at the bottom of the extraction column above the discharge of the organically loaded sodium hydroxide solution, is 0.62 kg/h, and the aqueous sodium hydroxide solution is pumped in at a rate of 4.74 kg/h. The ratio of the two phases, i.e. product stream II:aqueous NaOH phase= 1:7,65.

The results and the composition of the organic product streams are shown in the following Table:

TABLE I

| Component (%) | DMP Feed | Product Stream I | Product Stream II | Product Stream III | Product Stream VI |
|---|---|---|---|---|---|
| MeOH | 67.9 | 55.7 | 45.8 | 0.29 | 21 |
| Acetone | 31.1 | 20.3 | 17.3 | 9.5 | 9.9 |
| IPM | 0 | 0 | 12 | 32 | 42.2 |
| DMP | 0 | 19 | 21.1 | 56.1 | 26.4 |
| Water | 0 | 3.8 | 2.7 | 0.3 | 0 |
| NaOH | 0 | 0 | 0 | 0 | 0 |
| High b.p. compds. | 0 | 0 | 0 | 0 | 0 |
| Weight of stream (kg) | 2.211 | 3.091 | 3.091 | 1.16 | 0.88 |

The experimental results show the advantages of the process according to the invention in the extraction. The recovery rate of both IPM and DMP is quantitative, which means that when the units are properly operated there are no losses due to back-cleavage of DMP (or IPM) with water to form methanol and acetone. The product stream III that is formed, which consists substantially of DMP, IPM and acetone, can be separated directly in the IPM distillation

EXAMPLE 3

Distillation I of the DMP-IPM solution (product stream III)

The DMP-IPM mixture is distilled in a distillation column consisting of a feed pump, circulatory evaporator with level regulation, a 2 m DN 80 column with DX packings, and a condensate splitter. The mixture is fed in at the middle of the column.

The mixture separates as follows:

TABLE II

| Component (%) | Product Stream III | Product Stream IV | Product Stream V: IPM Phase | Product Stream V: Aqueous Phase | (IPM + Aqueous) Phase |
|---|---|---|---|---|---|
| MeOH | 0.18 | 0 | 0.38 | 10.6 | 0.58 |
| Acetone | 7.89 | 11.27 | 0.46 | 0.49 | 0.46 |
| IPM | 32.8 | 2.5 | 98.7 | 0.65 | 96.8 |
| DMP | 58 | 85.1 | 0 | 0 | 0 |
| Water | 1.17 | 0.65 | 0.46 | 88.12 | 2.2 |
| High b.p. compds. | 0.4 | 0.65 | 0 | 0.12 | 0 |

It can be seen from the quantitative data that the individual components behave in a chemically inert manner to one another during the distillation. It can also clearly be seen from the figures for the individual IPM-containing product streams III, IV and V that the water content in the product stream IV intended for the pyrolysis can be drastically reduced by removing primarily water as an IPM-water azeotrope as distillate I. The back reaction of DMP with water in the pyrolysis stage and thus a corresponding loss of yield can be prevented by this procedure.

EXAMPLE 4

DMP is fed into the apparatus described in Example 1 in order to investigate how the conversion, yield, selectivity, LHSV and the catalyst esterification as a measure of the catalyst ageing behave as a function of the reaction temperature and feed rate. The characteristic reaction data were determined in order to evaluate the catalyst ageing after a start-up phase of more than 70 hours' continuous operation.

The following Table III shows the behaviour of the conversion, yield, selectivity amd LHSV of the reaction of DMP to IPM using 2-ethylhexanoic acid as catalyst at 130° C.

TABLE III

| Time/h | % Conversion | % Selectivity | % Yield | LHSV 1/h/1 Cat. |
|---|---|---|---|---|
| 71.5 | 74.4 | 92.9 | 69.1 | 0.61 |
| 93.5 | 73.3 | 94.5 | 69.2 | 0.67 |
| 117.5 | 73.3 | 98.8 | 72.5 | 0.72 |
| 141.5 | 74.2 | 96.4 | 71.5 | 0.83 |

It can be seen from Table III that even after more than 140 hours' reaction time there is no decrease in selectivity and conversion. The increase in LHSV is explained at constant DMP feed by the decrease in 2-ethylhexanoic acid (formation of methyl 2-ethylhexanoate) with increasing reaction time. In order to obtain a better understanding the change in concentration of both components was determined in the aforedescribed experiment by quantitative measurement of 2-EHS and the corresponding methyl ester as a function of the reaction time, and is expressed in g catalyst. The results of these investigations are shown in the following Table IV.

TABLE IV

Conversion of DMP to IPM using 2-ethylhexanoic acid as catalyst at 130° C.

| Time/h | % Conversion | % Selectivity | % Yield | g Cat. |
|---|---|---|---|---|
| 71.5 | 74.4 | 92.9 | 69.1 | 227.1 |
| 93.5 | 73.3 | 94.5 | 69.2 | 206.4 |
| 117.5 | 73.3 | 98.8 | 72.5 | 182.8 |
| 141.5 | 74.2 | 96.4 | 71.5 | 164.8 |

EXAMPLE 5

In order to be able to evaluate the influence of the reaction temperature, the procedure in Example 4 is repeated except that the chosen reaction temperature is 110° C. Here too a quantitative increase in LHSV at constant real DMP feed is found due to the connection between the reaction time and the increasing proportion of the corresponding methyl ester of the catalyst acid.

TABLE V

Conversion of DMP to IPM using 2-ethylhexanoic acid as catalyst at 110° C.

| Time/h | % Conversion | % Selectivity | % Yield | LHSV 1/h/1 Cat. |
|---|---|---|---|---|
| 53 | 73.8 | 91.6 | 67.6 | 0.5 |
| 100 | 73.8 | 92.4 | 68.2 | 0.54 |
| 146 | 72.9 | 94.1 | 68.6 | 0.61 |
| 199 | 73.9 | 91.7 | 67.7 | 0.66 |

Table VI shows, instead of the LHSV, the actual content of the catalyst in g in the pyrolysis apparatus.

TABLE VI

Conversion of DMP to IPM using 2-ethylhexanoic acid as catalyst at 110° C.

| time/h | % Conversion | % Selectivity | % Yield | g Cat |
|---|---|---|---|---|
| 73.0 | 73.8 | 91.6 | 67.6 | 263.6 |
| 100.0 | 73.8 | 92.4 | 68.2 | 248.6 |
| 146.0 | 72.9 | 94.1 | 68.6 | 223.8 |
| 199.0 | 73.9 | 91.7 | 67.7 | 207 |

Further variations and modifications of the foregoing will be apparent to those skilled in the art and are intended to be encompassed by the claims.

German Priority Application 100 29 599.1 is relied on and incorporated herein by reference.

We claim:

1. A process for the production of an unsaturated ether represented by the formula (1)

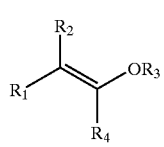

(1)

by pyrolysis of an acetal or ketal represented by the formula (2)

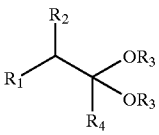

(2)

wherein
$R_1$=H or alkyl with 1–8 C atoms;
$R_2$=H, $CH_3$—, $C_2H_5$—, or Cl—;
$R_3$=alkyl with 1–8 C atoms;
$R_4$=H, $CH_3$—, $C_2H_5$—, $C_3H_7$—,
and $R_1$ and $R_4$ may be joined to form a 5-, 6-, or 7-membered ring, comprising:
a) in a ketalization reaction, ketalizing, in the presence of an acid catalyst, the corresponding acetal or ketal of the formula (2), which is formed by reacting the corresponding alcohol of the formula (3)

$R_3$—OH     (3)

wherein $R_3$ denotes space-holders for the substituents $R_3$ specified above, with an aldehyde or ketone of the formula (4)

(4)

wherein $R_1$, $R_2$ and $R_3$ denote space-holders for the substituents $R_1$, $R_2$ and $R_3$ specified above, to produce a product stream I, and
b) combining the product stream I resulting from the ketalization reaction, which includes a mixture of components of the formulae (2), (3), (4) and water, with recycle product stream VI of the ketal or acetal pyrolysis, which includes a ketal or acetal, the desired unsaturated ether of the formula (1) as product, and the alcohol of the formula (3), to form the product stream II, and
c) separating water and alcohol from a product stream II and extracting combined organic product streams of product stream II with an aqueous alkaline solution and thereby forming an organic product stream III by this extraction, which includes a mixture of the corresponding ketal or acetal, the desired unsaturated ether as product, and residual amounts of the aldehyde or ketone of the formula (4) and water, and
d) distilling product stream III and thereby isolating the desired unsaturated ether product as a product stream V and obtaining a product stream IV as the distillate residue, and
e) pyrolyzing said distillation residue which is produced in d), which contains the acetal of the formula (2) and the corresponding carbonyl compound of the formula (4), in a high boiling point organic carboxylic acid at 80° C.–300° C. to obtain recycle product stream VI, which contains in addition to the desired unsaturated ether also unreacted ketal and/or acetal and the corresponding alcohol, which is recycled to the extraction of c) and is combined with the product stream I from the ketalization.

2. The process according to claim 1, wherein the pyrolysis e) of the organic product stream IV consisting of ketal and/or acetal of formula (2) and the corresponding carbonyl compound of formula (4) is carried out in the presence of an organic carboxylic acid with 5–20 carbon atoms.

3. The process according to claim 2, wherein during the pyrolysis e) the carboxylic acids used as catalyst for the pyrolysis form over a prolonged reaction time esters with alcohol that is released, with the result that without discharge there is a noticeable increase of the corresponding ester as well as the carboxylic acid, without any pronounced influence on the yield and conversion of the pyrolysis reaction.

4. The process according to claim 2, wherein carboxylic acids monosubstituted or disubstituted in the 2-position are used as organic carboxylic acid and the pyrolysis e) takes place at temperatures between 80° C. and 300° C. in the liquid phase, by metering a product stream IV of ketal of the formula (2), and/or acetal and the corresponding carbonyl compound of the formula (4) to the liquid, organic carboxylic acid, and a distillate is obtained that contains, in addition to unreacted ketal (2), the desired ether (1), the carbonyl compound (4) and the alcohol (3) cleaved by the pyrolysis.

5. The process according to claim 4, wherein the product stream VI obtained after the pyrolysis e) is combined with the organic product stream I of the ketalisation and the extraction is performed with an aqueous alkaline solution, an organic product stream III being formed after the extraction that, apart from traces of water, is essentially free of alcohol (3) and consists essentially of ketal of formula (2) and ether of formula (1).

6. The process according to claim 1, wherein
   a) the desired unsaturated ether of formula (1) is obtained by distillation of the product stream III,
   b) said ether is obtained as the distillate, leaving an essentially water-free product stream IV, which contains ketal of the formula (2) and carbonyl compound of the formula (4), and
   c) the product stream IV is fed directly to the pyrolysis unit, where said ketal is transformed to the corresponding ether.

7. The process according to claim 1, wherein the pyrolysis is carried out as a thermal pyrolysis in the absence of an organic catalyst base.

8. The process according to claim 1, wherein the preparation of the ketal of the formula (2) is performed by ketalization of the corresponding carbonyl compound of the formula (4) with an alcohol of the formula (3) in the presence of an acidic ion exchanger, where the ratio of carbonyl compound to alcohol of between 5:1 and 1:5 and the ketalization takes place in a temperature range between −30° C. and +30° C.

9. The process according to claim 1, wherein DMP is produced by ketalization of acetone with methanol and isopropenyl methyl ether is produced by pyrolysis of a solution containing DMP and acetone in the presence of an organic carboxylic acid.

10. The process according to claim 1, wherein the IPM selectivity is at least 90%.

11. The process according to claim 1, wherein the IPM selectivity is more than 95%.

* * * * *